US009044387B2

(12) United States Patent
Zhao et al.

(10) Patent No.: US 9,044,387 B2
(45) Date of Patent: Jun. 2, 2015

(54) VAGINAL LUBRICANT COMPRISING HYALURONIC ACID

(75) Inventors: Xiaobin Zhao, Cambridge (GB); Kevin Alexander Burd, Burntisland (GB)

(73) Assignee: British Biocell International Limited, Cardiff (GB)

( * ) Notice: Subject to any disclaimer, the term of this patent is extended or adjusted under 35 U.S.C. 154(b) by 435 days.

(21) Appl. No.: 12/742,357

(22) PCT Filed: Nov. 19, 2008

(86) PCT No.: PCT/GB2008/051086
§ 371 (c)(1),
(2), (4) Date: Jul. 16, 2010

(87) PCT Pub. No.: WO2009/066102
PCT Pub. Date: May 28, 2009

(65) Prior Publication Data
US 2010/0284937 A1 Nov. 11, 2010

(30) Foreign Application Priority Data

Nov. 19, 2007 (GB) .................................. 0722507.1

(51) Int. Cl.
| | | |
|---|---|---|
| A61K 31/722 | (2006.01) | |
| A61P 15/02 | (2006.01) | |
| A61K 9/00 | (2006.01) | |
| A61P 15/08 | (2006.01) | |
| A61K 31/728 | (2006.01) | |

(52) U.S. Cl.
CPC .............. *A61K 9/0034* (2013.01); *A61K 31/722* (2013.01); *A61K 31/728* (2013.01)

(58) Field of Classification Search
CPC ....... A61L 27/20; A61L 27/34; A61L 29/085; A61L 15/28; A61L 24/08; A61L 31/042; A61Q 19/00; A61Q 17/04; A61Q 19/08
See application file for complete search history.

(56) References Cited

U.S. PATENT DOCUMENTS

| | | | | |
|---|---|---|---|---|
| 2,585,546 | A | | 2/1952 | Hadidian et al. |
| 4,303,676 | A | | 12/1981 | Balazs |
| 5,819,730 | A | * | 10/1998 | Stone et al. ............. 128/203.21 |
| 5,897,880 | A | * | 4/1999 | Drizen et al. ............ 424/488 |
| 6,465,626 | B1 | * | 10/2002 | Watts et al. ............ 536/20 |
| 7,094,766 | B1 | * | 8/2006 | Gilchrest et al. ........... 514/44 R |
| 7,125,860 | B1 | * | 10/2006 | Renier et al. ............ 514/54 |
| 2004/0247632 | A1 | * | 12/2004 | Cattaneo ............ 424/401 |
| 2006/0166928 | A1 | | 7/2006 | Moon et al. |
| 2006/0204557 | A1 | * | 9/2006 | Gupta et al. ............ 424/443 |

FOREIGN PATENT DOCUMENTS

| | | | |
|---|---|---|---|
| CN | 1660130 | A | 8/2005 |
| EP | 1 444 984 | A1 | 8/2004 |
| FR | 2 478 468 | A1 | 9/1981 |
| JP | S63218617 | A | 9/1988 |
| JP | 01 190614 | A | 7/1989 |
| JP | 01190614 | A * | 7/1989 .................. 424/401 |
| JP | 01190614 | A * | 7/1989 .................. 424/401 |
| WO | WO-9843614 | A1 | 10/1998 |
| WO | WO-2008/003321 | A2 | 1/2008 |
| WO | WO-2008/094910 | A2 | 8/2008 |

OTHER PUBLICATIONS

JP 01190614, published Jul. 31, 1989. Inventor Miyamoto Tatsu.*
JP 01190614 A. Ota et al. Published Jul. 1989, abstract translation.*
JP 01190614A. Ota et al. Published Jul. 1989, full translation.*
JP01190614A. Ota et al. Published Jul. 1989, abstract translation.*
JP01190614A. Ota et al. Published Jul. 1989, full translation.*
Kutteh, W.H., et al., "Vaginal Lubricants for the Infertile Couple: Effect on Sperm Activity", International Journal of Fertility, Allan Press, Inc., Kansas, U.S., vol. 41, No. 4, Jan. 1, 1996, pp. 400-404, XP000870083.
Villa Riva, A., "International Search Report", for PCT/GB2008/051086 as mailed Apr. 27, 2009, 3 pages.
Tømmeraas, K., et al., "Kinetics of Hyaluronan Hydrolysis in Acidic Solution at Various pH Values", Biomacromolecules 2008, 9, 1535-1540.
Na, Zhang, "Chinese Office Action" with English translation, as mailed Nov. 2, 2011, 18 pages.
Crescenzi, V., et al., "New Cross-Linked and Sulfated Derivatives of Partially Deacetylated Hyaluronan: Synthesis and Preliminary Characterization", 2002 Wiley Periodicals, Inc. Biopolymers 64: 86-94, 2002.
Crescenzi, V., et al., "NMR Structural Study of Hydrogels Based on Partially Deacetylated Hyaluronan", Macromolecular Bioscience, 2002, vol. 2, No. 6, pp. 272-279.
Cifonelli J.A., "Mucopolysaccharides Hydrolysis", Carbohydrate Res., 2, 1966, pp. 150-161.
Maleki, Atoosa et al., "Effect of pH on the Behavior of Hyaluronic Acid in Dilute and Semidilute Aqueous Solutions", Macromol. Symp., 2008, 274, pp. 131-140.
EPO Examination Report issued May 28, 2014.
Farwick M. et al., Low Molecular Weight Hyaluronic Acid: Its Effects on Epidermal Gene Expression and Skin Ageing; SOFW Journal; 134; Nov. 2008.
Sanchez, R. et al., Use of chitin, chitosan and acylated derivatives as thickener agents of vegetable pils for bio-lubricant applications; 85: 705-714 (2011).
Huang, Y., et al., "To Explore the Effect of Chitosan in Prevention Recurrence of Tubal Adhesion," Chinese Journal of Misdiagnostics, vol. 6, No. 19, Oct. 2006, pp. 3685-3686.

* cited by examiner

*Primary Examiner* — Audrea Buckley
(74) *Attorney, Agent, or Firm* — Winstead PC

(57) ABSTRACT

A vaginal lubricant comprising high molecular weight hyaluronic acid combined with low molecular weight hyaluronic acid and/or chitosan which has improved stability and which has applications in, for example, maintaining and/or promoting sperm motility.

31 Claims, 1 Drawing Sheet

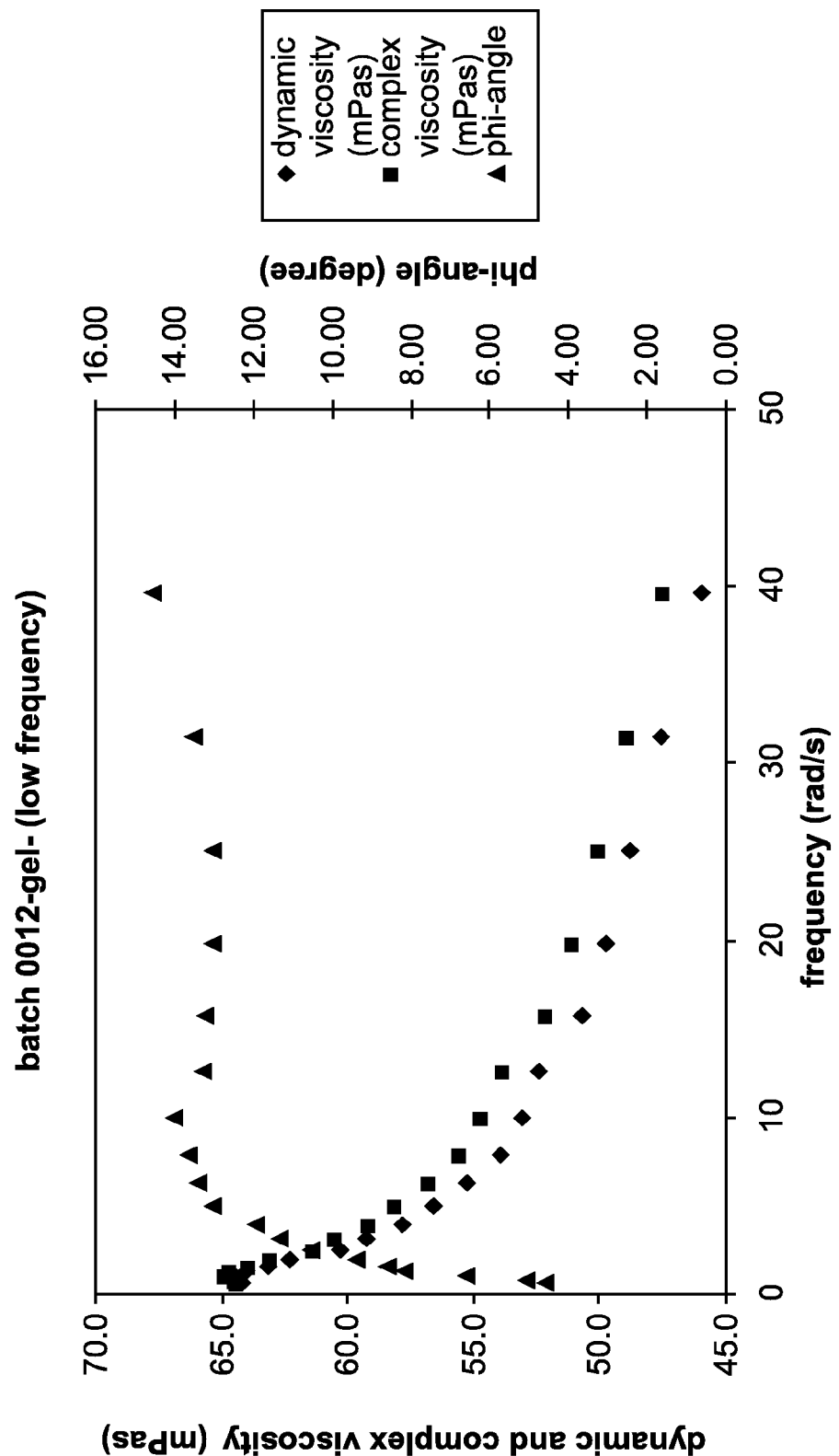

VAGINAL LUBRICANT COMPRISING HYALURONIC ACID

FIELD OF INVENTION

This invention relates to a personal lubricant and in particularly to a vaginal lubricant based on the natural viscoelastic biopolymer, hyaluronic acid (HA). The vaginal lubricant generally includes HA having a defined molecular weight distribution. The HA is advantageously produced from the micro-organism *Bacillus subtilis*.

BACKGROUND OF THE INVENTION

Hyaluronic acid (also called Hyaluronan or sodium hyaluronate), abbreviated as HA, is a non-sulfated glycosaminoglycan distributed widely throughout connective, epithelial, and neural tissues. It is one of the chief components of the extracellular matrix and contributes significantly to cell proliferation and migration. HA may also be involved in the progression of some malignant tumors. The average 70 kg man has roughly 15 grams of HA in his body, one third of which is degraded and synthesised every day.

Lubricants for Joints

HA is a major component of the synovial fluid and is found to increase the viscosity of the synovial fluid. Along with lubricin, it is one of the main lubricating components of synovial fluid. HA is an important component of articular cartilage, in which it coats each cell (chondrocyte). When aggrecan monomers bind to HA in the presence of link protein, large highly negatively charged aggregates are formed. These aggregates imbibe water and are responsible for the resilience of cartilage (its resistance to compression). The molecular weight (size) of HA in cartilage decreases with age, however the amount of HA in cartilage increases with age.

Biomatrix Components for Skin Tissue Repair

HA is a major component of skin, where it is involved in tissue repair. When skin is excessively exposed to UVB rays, the HA present in skin acts as a free radical scavenger, absorbing free radicals. The skin becomes inflamed (sunburn) and the cells in the dermis stop producing as much HA. The rate of its degradation is also increased. HA degradation products also accumulate in the skin after UV exposure.

While it is abundant in extracellular matrices, HA also contributes to tissue hydrodynamics, movement and proliferation of cells, and participates in a number of cell surface receptor interactions, notably those including its primary receptor, CD44. Upregulation of CD44 itself is widely accepted as a marker of cell activation in lymphocytes. HA's contribution to tumor growth may be due to its interaction with CD44. CD44 participates in cell adhesion interactions required by tumor cells. Although HA binds to CD44, there is evidence showing that HA degradation products transduce their inflammatory signal through Toll-like receptor 2 (TLR2), TLR4 or both TLR2 and TLR4 in macrophages and dendritic cells. TLR and HA play a role in innate immunity.

Structure and Synthesis of HA

The structure of HA is well characterized. It is composed of repeated units of disaccharide of D-glucuronic acid and D-N-acetylglucosamine, linked together via alternating β-1,4 and β-1,3 glycosidic bonds. HA is typically up to 25,000 disaccharide units in length. The molecular weight of HA can range from 5,000 to 20,000,000 in vivo. The average molecular weight in human synovial fluid is 3 to 4 million and HA purified from human umbilical cord is typically 3,140,000 Da.

HA is synthesized by a class of integral membrane proteins called HA synthases, of which vertebrates have three types: HAS1, HAS2, and HAS3. These enzymes lengthen HA by repeatedly adding glucuronic acid and N-acetylglucosamine to the nascent polysaccharide as it is extruded through the cell membrane into the extracellular space. Commercially, HA can be produced from animal sources, for example, from rooster combs, umbilical cords, and from the cartilage of joints. Alternatively HA may be obtained through fermentation. The average molecular weight of HA varies according to the source from which it is obtained. Generally the molecular weight of HA is 60,000 to 14,000,000.

Commercially available HA is generally produced from animal sources or from bacterial sources. Generally HA is obtained from bacterial sources through fermentation processes. The fermentation processes involve many steps including HA synthesis, separation and purification. The purity of HA is dependent on the source it is obtained from, in particular it is dependent on the bacteria used and the process techniques. The purity of HA has a significant influence on its stability.

Biocompatibility and Medical Applications of HA

HA is nontoxic, non-immunogenic and biodegradable. HA is degraded by a family of enzymes called hyaluronidases. In humans, there are at least seven types of hyaluronidase-like enzymes, several of which are tumor suppressors. The degradation products of HA, the oligosaccharides and very low molecular weight HA, exhibit pro-angiogenic properties. In addition, recent studies have shown that HA fragments, rather than high molecular HA components, can induce inflammatory responses in macrophages and dendritic cells in tissue injury and in skin transplant rejection.

The first HA biomedical product, Healon, was developed in the 1970s and 1980s and is approved for use in eye surgery (i.e., corneal transplantation, cataract surgery, glaucoma surgery and surgery to repair retinal detachment). Other biomedical companies also produce brands of HA for ophthalmic surgery.

HA is also used to treat osteoarthritis of the knee. Such treatments, called viscosupplementation, are administered as a course of injections into the knee joint and are believed to supplement the viscosity of the joint fluid thereby lubricating the joint, cushioning the joint and producing an analgesic effect. It has also been suggested that HA has positive biochemical effects on cartilage cells. The molecule weight is varied from 750,000 to 2 million and some of the preparation in which HA is lightly crosslinked. However, some placebo controlled studies have cast doubt on the efficacy of HA injections, and HA is recommended primarily as a last alternative to surgery. Oral use of HA has been lately suggested although effectiveness still needs to be demonstrated. Some preliminary clinical studies suggest that oral administration of HA has a positive effect on osteoarthritis.

Due to its high biocompatibility and its common presence in the extracellular matrix of tissues, HA is gaining popularity as a biomaterial scaffold in tissue engineering research.

In some cancers, HA levels correlate well with malignancy and poor prognosis. HA is thus often used as a tumor marker for prostate and breast cancer. It may also be used to monitor the progression of the disease.

HA may also be used postoperatively to induce tissue healing, notably after cataract surgery. Current models of wound healing propose that larger polymers of HA appear in the early stages of healing to physically make room for white blood cells, which mediate the immune response.

Personal Lubricant

A natural acidic lubricating fluid is normally present in the vagina and during sexual arousal an increased amount of the fluid is produced. The function of production of sufficient vaginal lubrication may be impaired, causing vaginal tissue to become dry and irritated due to a number of causes including decreased estrogen levels during the menopause or after surgical removal of ovaries and after radiation therapy. This may result in pain during sexual intercourse and/or bleeding during sexual intercourse. Oral contraceptives and certain medications such as antihistaminics, antidepressants, blood pressure, and cardiac medicines can also contribute to vaginal dryness. Additionally, psychological conditions including stress, fatigue and anxiety may impede production of the natural lubricant. A combination of hormonal and psychological factors may induce dryness temporarily after childbirth particularly if the mother is breastfeeding. Stress for those couples under IVF treatment for conceiving is another particular example.

Common personal lubricants such as silicone and those sold under the Trade Marks K-Y Jelly® and Vaseline® are mainly based on synthetic substances such as silicone, petroleum. Commercially available lubricants containing glycerin are spermicidal and impede sperm motility. Even at low concentrations ingredients such as glycerin are associated with such spermicidal effects. Accordingly, such commercially available vaginal lubricants are not recommended for women seeking to conceive.

Personal lubricants comprising HA as the lubricating component are known for the treatment and relief of vaginal dryness.

HA has been found to be useful in IVF treatment. It is a normal component of mammalian follicular, oviductal, and uterine fluids (Lee and Ax 1984, Suchanek et al 1994, Rodriguez-Martinez et al 1998). Physiological concentrations of hyaluronan in these fluids, for instance, range from 0.04 to 1.83 mg/mL, 16 to 39% of all glycosaminoglycans (Kano et al 1998), which in turn provides a high viscosity environment in the oviduct and uterus. In vivo, it is known that hyaluronan supports ovulation and assists in sperm selection during the fertilization process.

Commercially available HA is a natural biodegradable polymer. It is especially unstable under extreme conditions-such as high temperature, high pH or low pH (alkaline and acidic condition), or in the presence of free radicals or free radical precursors. Under such conditions HA having a relatively high molecular weight, for instance 1 to 3 million tends to degrade into small HA fragments. In addition, the presence of impurities such as trace heavy metals like $Fe^{2+}$, $Fe^{3+}$, $Cr^{3+}$, $Cu^{2+}$, $Al^{3+}$ etc will accelerate the degradation process.

DISCLOSURE OF INVENTION

One objective of the present invention is to provide a natural, biocompatible personal lubricant for moisturizing and lubricating the vagina.

A further objective of the present invention is to provide a vaginal lubricant, having a viscosity suitable for enhancing the lubricity of the vagina at a pH of 3.8 to 4.5 (as commonly associated with the vaginal environment).

Although vaginal lubricants comprising HA are known, they are associated with several disadvantages as detailed above. In particular the duration of action of known vaginal HA lubricants is limited and unpredictable. In addition, the stability of known vaginal HA lubricants upon storage is unpredictable.

The vaginal environment is acidic, generally having a pH of around 3.8 to 4.5. Known, commercially available, HA undergoes significant degradation in such acid environments, in particular at body temperature (approximately 37° C.). Such degradation leads to a significant reduction in molecular weight of the HA and a corresponding decrease in its viscosity. Accordingly, the lubricating effect of known HA vaginal lubricants is generally short and the duration of the lubricating effect of known HA vaginal lubricants is generally not predictable. In addition, known HA vaginal lubricants may degrade during storage, and thus be ineffective upon application. The shelf life of known HA vaginal lubricants may be short and the shelf-life of known HA vaginal lubricants is generally unpredictable.

Commercially available HA is unstable, and to degrade under high temperature or acid or alkaline conditions. Under such conditions, commercially available HA degrades into small HA fragments. Due to the acidic nature of the vaginal environment, where the pH is normally around 3.8 to 4.5, commercially available HA will significantly degrade leading to a reduction in molecular weight and an associated reduction in viscosity. As such, the lubricating effects of known HA vaginal lubricants are associated with a limited duration. However, increasing the concentration of HA in such lubricants results in a decrease in associated sperm motility. Accordingly, known vaginal HA lubricants should not be used by women seeking to conceive. In addition, known vaginal HA lubricants may degrade upon storage leading to a limited and unpredictable shelf-life.

According to the present invention, a combination of different molecular weight components of HA is used to optimize the duration of the lubricating effect of the vaginal lubricant of the present invention and to maintain and/or increase the motility of sperm that come into contact with the vaginal lubricant. In addition, the lubricant of the present invention particularly increases or maintains the motility of robust sperm compared to less robust sperm, thus promoting the chances of conception. Surprisingly the combination of high and low molecular weight HA components reduces the degradation of HA, meaning that the shelf-life of the vaginal lubricant of the present invention is maximized and that the stability of the vaginal lubricant of the present invention upon storage is predictable. The reduction in the degradation of HA in the vaginal lubricant of the present invention also results in the duration of the lubricating effects thereof being maximized even following exposure to acidic pH such as those associated with the vaginal environment.

Another objective of the present invention is to provide a vaginal lubricant that increases or maintains the motility of sperm that comes into contact therewith. Women seeking to conceive, and particularly those women undergoing IVF treatment, may use a vaginal lubricant of this type. The use of such a lubricant may enhance the success rate of IVF treatment.

It is a further objective of the present invention to provide a vaginal lubricant which is non-spermicidal and does not impede sperm motility.

According to a first aspect of the present invention there is provided a vaginal lubricant comprising high molecular weight HA having a molecular weight of 750,000 to 3,000,000 and a low molecular weight component having a molecular weight of 1,000 to 500,000 wherein the ratio of high molecular weight HA to the low molecular weight component is 9:1 w/w to 1:9 w/w.

Typically the high molecular weight HA has a molecular weight of 750,000 to 2,000,000, suitably 750,000 to 1,400, 000. The high molecular weight component may have a molecular weight of 800,000 to 1,200,000.

Generally the low molecular weight component has a molecular weight of 10,000 to 750,000; suitably 10,000 to 500,000, suitably 150,000 to 250,000. Alternatively, the low molecular weight component has a molecular weight of 25,000 to 60,000.

The average molecular weight of the high molecular weight HA is suitably 800,000 to 1,200,000, generally around 1,000,000. The average molecular weight of the low molecular weight component is suitably 25,000 to 60,000; typically 40,000 to 60,000; generally around 50,000.

The low molecular weight component may be HA, chitosan or any other amino-containing molecule (natural or synthetic) not specifically excluded herein. The low molecular weight component may be an amino-containing polysaccharide or amino acid. The low molecular weight component molecules can be associated with HA to coat HA at a molecular level in order to stabilise HA. Generally the low molecular weight component is chitosan or HA. Advantageously the low molecular weight component is HA.

The ratio of high molecular weight HA to chitosan is suitably 3:1 w/w to 1:3 w/w. The exact ratio of high to low molecular weight component is dependent on the desired properties of the vaginal lubricant. If it is advantageous for the lubricant to provide high bioactive properties, (in particular, high free-radical scavenging properties), the ratio of high to low molecular weight components should be relatively low, for instance 1:5 to 2:5. If it is advantageous for the lubricant to have a high viscosity, the ratio of high to low molecular weight components should be relatively high, for instance 5:1 to 5:2. The particular beneficial ratio may be determined experimentally depending on the desired properties of the lubricant.

According to one embodiment, the vaginal lubricant comprises 0.1 to 1 weight % high molecular weight HA. Typically the vaginal lubricant comprises 0.1 to 1 weight % low molecular weight component.

The high molecular weight HA is believed to adjust the viscosity of the vaginal lubricant and may act as a barrier to low quality sperm due to its viscosity while the low molecular weight component is believed to act as a bioactive molecule. The low molecular weight component is believed to facilitate sperm motility and to act as a free-radical scavenger.

As such, the lubricant of the present invention promotes the selection of good quality sperm thus increasing the chances of conception.

The vaginal lubricant of the present invention generally has a viscosity of 100 to 1,000,000 mPa·s; preferably a viscosity of 1,000 to 500,000 mPa·s.

According to one embodiment, the vaginal lubricant comprises 0.1 to 1% HA and has a viscosity of 2 to 1,000 mPa·s.

The vaginal lubricant of the present invention may have a pH of 2.4 to 7.8; suitably 5.8 to 7.4; typically 6.0 to 7.8; more suitably 6.5 to 7.4.

Generally the vaginal lubricant of the present invention is physiologically neutral and has a pH of 6.5 to 7.4.

The vaginal lubricant of the present invention may comprise a phosphate buffered solution to ensure and maintain a particular pH range.

Typically, the HA of the lubricant of the present invention is obtained from animal sources or from bioprocesses, including via bacterial or enzyme synthesis. Suitably, the HA of the lubricant of the present invention is obtained from fermentation or enzymatic synthesis.

The vaginal lubricant of the present invention preferably comprises HA produced from the micro-organism *Bacillus subtilis*. Suitably all of the HA of the vaginal lubricant of the present invention is produced from the micro-organism *Bacillus subtilis*.

The purity of HA is partially or wholly dependent on its source and its method of production. The purity of HA used in known vaginal lubricants is limited, typically the purity of such HA is less than 85%, typically less than 70%. In contrast, the purity of HA produced from the micro-organism *Bacillus subtilis* is generally above 85%, generally 90% or more. Typically HA produced from the micro-organism *Bacillus subtilis* has a moisture content of around 10 to 15%. In particular, the HA used in the lubricant of the present invention suitably includes a heavy metal impurity level of less than 10 ppm; advantageously less than 5 ppm.

*Bacillus subtilis* is a Gram-positive, catalase-positive bacterium commonly found in soil. The production of HA from *Bacillus subtilis* is known in the art. However, HA produced from *Bacillus subtilis* has not previously been used in vaginal lubricants.

The combination of high and low molecular weight components and the purity of the HA used mean that the vaginal lubricant of the present invention is very stable compared to known HA vaginal lubricants. In particular, the lubricant of the present invention is stable upon exposure to extremes of temperature and extremes of pH, such as increased temperatures and acid or alkaline conditions.

The HA of the lubricant of the present invention does not hydrolyse to any significant extent upon exposure to the pH such as that associated with the acidic vaginal environment. As such, the lubricant of the present invention does not hydrolyse to any significant extent upon or following application of the personal lubricant of the present invention. Generally, the lubricant of the present invention does not significantly degrade upon contact with conditions commonly associated with the vaginal environment for 6 to 12 hours, which is a pH of 3.8 to 4.5 and a temperature of approximately 35 to 37° C. Typically the lubricant of the present invention degrades less than 10 to 25% upon such contact, generally 10 to 20%, suitably 10 to 15%. In contrast, known HA vaginal lubricants generally significantly degrade upon such contact, typically more than 25% generally 30 to 40%.

The viscosity of the vaginal lubricant is generally maintained for at least 6 hours upon contact with conditions commonly associated with the vaginal environment.

According to one embodiment, the vaginal lubricant of the present invention comprises acid treated HA. Typically, a proportion of the high molecular weight HA has been acid treated. Alternatively, a proportion of the HA making up the low molecular weight component has been acid treated.

Unexpectedly, the addition of some acid treated HA to the vaginal lubricant can improve the stability of the HA contained therein, in particular at a pH around 3.8 to 4.5 and/or at increased temperature. The acid treatment is generally carried out by de-acetylation of HA in acid, such as nitric acid, to generate free amino groups, which will further stabilize the HA in acidic conditions.

The lubricant of the present invention suitably comprises a high molecular weight HA component, a low molecular weight component and acid treated HA.

According to one embodiment, low molecular weight HA may make up the low molecular weight component of the vaginal lubricant of the present invention. In addition the vaginal lubricant may comprise low molecular weight chitosan (LMW chitosan). Where the low molecular weight component comprises low molecular weight HA, the addition of LMW chitosan unexpectedly increases the stability of the vaginal lubricant of the present invention.

The lubricant of the present invention suitably comprises a high molecular weight HA component, a low molecular weight HA component and chitosan.

Typically, the addition of chitosan improves the stability of the vaginal lubricant at a pH around 3.8 to 4.5. In particular, the addition of chitosan improves the water stability of the vaginal lubricant. The chitosan typically has a relatively low molecular weight compared to the high molecular weight HA component of the personal lubricant of the present invention.

The chitosan suitably has a molecular weight of 1,000 to 750,000. Generally the chitosan has a molecular weight of 1,000 to 500,000; suitably the chitosan has a molecular weight of 10,000 to 500,000; typically the chitosan has a molecular weight of 10,000 to 100,000. Suitably the chitosan has an average molecular weight of 30,000 to 70,000, more suitably 40,000 to 60,000; advantageously around 50,000. The chitosan typically has an apparent viscosity of 20 to 200 mPa·s.

Typically, the vaginal lubricant comprises 0.1 to 1 weight % chitosan. More suitably the vaginal lubricant comprises 0.1 to 1 weight % high molecular weight HA. The vaginal lubricant generally comprises 0.1 to 1 weight % low molecular weight HA.

LMW chitosan is similar to deacetylated HA containing amino groups. LMW chitosan is water soluble and it will form an ionic complex with HA to resist acid degradation on HA.

The vaginal lubricant of the present invention may comprise other functional moieties such as DNA and/or one or more anti-oxidant compounds or compositions. Alternatively or additionally the vaginal lubricant may comprise nitric oxide releasing precursors such as one or more of nitric oxide synthase, arginine and citrulline and aspartic acid. In particular, the vaginal lubricant of the present invention may comprise highly polymerised DNA such as that obtainable from HTL in France. Typically the DNA concentration is between 0.1 to 5%, suitably between 0.1 to 1%.

Such functional moieties typically increase the antioxidant effect associated with the vaginal lubricant of the present invention and/or enhance the motility of sperm.

However, as noted above, LMW HA is a good free radical scavenger and therefore additional antioxidant compounds are not necessarily required. According to one aspect of the present invention the vaginal lubricant of the present invention does not comprise an anti-oxidant compound or composition.

The vaginal lubricant of the present invention may comprise medicaments, for instance medicaments useful in the treatment of sexually transferred diseases (STD). Suitable medicaments include anti-bacterial or anti-microbial substances, such as benzethonium chloride.

In another preferred embodiment of this invention, the gel may comprise additives to release nitric oxide such as natural nitric oxide precursors such as amino acids, for example L-Arginine, citrulline and aspartic acid Such additives may induce a warming effect upon application of the lubricant to the vagina thus increasing vaginal sensation in particular during sexual intercourse. In addition, the release of nitric oxide may have the effect of maintaining or enhancing sperm motility. As such the inclusion of nitric oxide releasing compounds may increase or maximize the chances of conception.

The vaginal lubricant typically comprises 0.1 to 10% of natural amino acids.

Typically the vaginal lubricant may comprise preservatives, in particular to ensure a low microbial content.

Generally the vaginal lubricant of the present invention may comprise other pharmaceutically acceptable adjuvants or excipients. For example, bioadhesives such as natural polymers for instance cellulose and, alginate or synthetic water soluble polymers such as PVA, PVP, polyethylene oxide, and polyacrylic acid.

The vaginal lubricant of the present invention may be in the form of a gel, foam, paste, liquid or spray.

In one embodiment, the lubricant, and particularly the low molecular weight component, does not comprise hydroxyethylcellulose, hydroxypropylcellulose, carboxymethylcellulose, dextran, mucin, lecithin or carrageenan.

According to a further aspect of the present invention there is provided a product comprising the vaginal lubricant as described above. The product may suitably be in the form of a syringe, capsule or sprayable container. In particular a single-use syringe or sprayable container including a single use nozzle to minimize or avoid the risk of cross-contamination.

Advantageously, the product of the present invention is in the form of a single use syringe or single use sprayable container. The vaginal lubricant may be sprayable due to the unique shear-thinning rheological properties of the combination of the high molecular weight HA and the low molecular weight component.

Typically, the product is in the form of a single use syringe having a volume of from 1 ml to 10 ml; typically 2 ml to 5 ml.

Alternatively, the product is in the form of a squeeze spray bottle comprising a spray nozzle, in particular a single-use spray nozzle. The vaginal lubricant of the present invention may be easily applied therefrom.

Advantageously the vaginal lubricant of the present invention is manufactured under sterile conditions, and the product comprising the vaginal lubricant of the present invention is manufactured under sterile conditions.

According to a further aspect of the present invention there is provided a method of providing vaginal lubrication comprising the steps of applying the vaginal lubricant described above to the vagina of a patient in need thereof.

According to a further aspect of the present invention there is provided the vaginal lubricant as described above for use in therapy.

According to a further aspect of the present invention there is provided the vaginal lubricant as described above for use in providing vaginal lubrication.

Preferably the method or use of providing vaginal lubrication includes the step of increasing or maintaining the motility of sperm.

According to a further aspect of the present invention there is provided a method of promoting conception comprising the steps of applying the vaginal lubricant described above to the vagina of a patient in need thereof.

According to a further aspect of the present invention there is provided the vaginal lubricant as described above for use in promoting conception.

According to a further aspect of the present invention there is provided a method of delivering a pharmaceutical or nutraceutical composition or the like comprising the steps of applying the vaginal lubricant as described herein to the vagina of a patient in need thereof.

According to a further aspect of the present invention there is provide a vaginal lubricant as described herein for use in delivering a pharmaceutical or nutraceutical composition or the like.

Providing vaginal lubrication increases the chances of conception. However, as noted above, known vaginal lubricants act as spermicides or greatly reduce the motility of sperm upon contact therewith. Accordingly, known vaginal lubricants reduce the likelihood of conception. In contrast, the vaginal lubricant of the present invention provides vaginal lubrication whilst maintaining or promoting sperm motility. Accordingly, the vaginal lubricant of the present invention increases the likelihood of conception. This increase in the likelihood of conception may be due to the lubricating effect of the lubricant of the present invention, as well as the bioactivity of HA. In addition, due to the combination of the molecular weight of the components thereof, the lubricating properties of the vaginal lubricant of the present invention are maintained for a relatively long duration compared to known lubricants, and the vaginal lubricant of the present invention is stable to exposure to conditions generally associated with the vaginal environment.

According to a further aspect of the present invention there is provided a method of manufacturing the vaginal lubricant of the present invention comprising the steps of:

combining high molecular weight HA having a molecular weight of 750,000 to 3,000,000 and a low molecular weight component having a molecular weight of 1,000 to 500,000, wherein the ratio of high molecular weight HA to the low molecular weight component is 9:1 w/w to 1:9 w/w.

Suitably the high molecular weight component has a molecular weight of 750,000 to 1,400,000. Typically the high molecular weight component has a molecular weight of 800,000 to 1,200,000. Suitably the low molecular weight component has a molecular weight of 10,000 to 500,000; typically the low molecular weight component has a molecular weight of 150,000 to 250,000. Typically the low molecular weight component has a viscosity of 20 mPa·s to 200 mPa·s.

Typically the method of the present invention proceeds at a temperature of 2 to 25° C.

Suitably the method of the present invention takes place under sterile conditions or under very clean conditions representing a low bioburden.

The present invention will now be described by way of example only and with reference to FIG. 1, which shows the dynamic and complex viscosities of formulation R0012 versus frequency.

EXAMPLES

Example 1

The ingredients detailed below were weighed out and combined under sterile conditions to formulate an HA gel having a pH of 6.5 to 7.5. The HA gel was then added to a syringe under sterile conditions to form a single-use syringe. Note that buffers such as sodium phosphate can be used in the preparation of the formulations.

The HMW HA used was eye drops grade or medical device grade having a molecular weight of 800,000 to 1,200,000, and was obtained from Novozymes A/S (Novozymes NS, Krogshoejvej 36, 2880 Bagsvaerd, Denmark. The LMW HA is sold under the trade name Resilin-200™, which has a molecular weight of 150,000 to 250,000, and which was obtained from Kyowa Hakko Bio Co., Ltd (Kyowa Hakko Europe GmbH, Am Wehrhahn 50, D-40211 Düsseldorf).

The various formulations prepared are shown in Table 1 below.

TABLE 1

| Sample No | LMW HA (g) | HMW HA (g) | Methylparaben solution (g) |
| --- | --- | --- | --- |
| B10 | 1.0 | 0.0 | 100 |
| B11 | 0.75 | 0.25 | 100 |
| B12 | 0.5 | 0.5 | 100 |
| B13 | 0.25 | 0.75 | 100 |
| B14 | 0.0 | 1.0 | 100 |

Safety and sperm motility testing were carried out as described below on samples B10 to B14 and using human sperm obtained from several donors.

A semen-preparation contact assay was carried out. Each preparation was assayed with semen from twenty different donors. Semen samples were incubated for 30 minutes at 37° C. to allow them to liquefy. Sperm concentration was determined using a CEROS computer-aided semen analyser (CASA, Hamilton Thorne) and diluted to approximately $25 \times 10^6$ sperm per ml with G-IVF™ PLUS (Vitrolife) which is a medium designed to support the preparation of male and female gametes and in vitro fertilisation. It contains the carbohydrates and amino acids required to support the fertilisation event. Semen at approximately $25 \times 10^6$ sperm per ml was incubated with 10% (v/v) 'preparation' or buffer control (90 µl semen and 10 µl 100% preparation/G-IVF™ PLUS) for 30 minutes at 37° C., and motility was then assessed using the CASA. A concentration of 10% for the preparations was selected to represent the concentrations of lubricant potentially present after mixing with cervical mucus and the ejaculate following intercourse.

For motility assessments, the percentages of motile sperm and progressively motile sperm were determined. For each replicate a minimum of 200 sperm were assessed. Any sperm moving faster than 5 µm per second was considered motile, while any motile sperm with average path velocity (VAP)≥25 µm per second and straightness (STR, calculated as [straight line velocity (VSL)/VAP]×100)≥80% was considered progressively motile. Assays were conducted in quadruplet (measuring four aliquots from each semen/sperm-preparation incubation) for each of the twenty donors. Four aliquots (approximately 800 cells assayed) provide a robust analysis.

To determine if the preparations had any effect on sperm motility, results were compared against G-IVF™ PLUS and Pré™. Pré™ is a vaginal lubricant, which can be used during assisted reproduction procedures such as intrauterine insemination and embryo transfer. Both G-IVF™ PLUS and Pré™ are commercially available products, and in the trials describe they provide control data. Once the data was obtained, motility reduction or enhancement was calculated. In order to determine if changes in motility were statistically significant Mann-Whitney-Wilcoxon two-tailed analyses were performed whereby p values of 0.05 or less indicated that differences were within 95% confidence limits and thus statistically meaningful.

To assess if the preparations had any differential effects on sperm of low, medium, or high quality, donors were grouped according to their original percentage motility. Those with <25%, 25-60%, and >60% motile sperm in their semen were considered low, medium and high motility respectively. Average changes in motility were calculated for each preparation in each motility group and data compared with G-IVF™ PLUS controls using Mann-Whitney-Wilcoxon two-tailed analyses.

A toxicity assessment was carried out using a TUNEL assay for DNA damage. The TUNEL assay (Fluorescein-FragEL kit, VWR) was performed for one donor (D053) immediately after isolated sperm-preparation contact assays.

Briefly, for each preparation, approximately 1×10⁶ sperm were smeared on poly-L-lysine coated slides, air dried, and fixed with methanol. Cells were permeabilised with protein kinase K and FITC-labelled nucleotides were added to DNA breaks using TdT enzyme. Unincorporated nucleotides were washed off before coverslip mounting with fluorescein-FragEL mounting media. 200 sperm cells were scored for DNA damage (fluorescence) for each preparation incubation. As a positive control, DNA damage was induced on an additional slide (smeared with approximately 1×10⁶ sperm incubated with G-IVF™ PLUS) through incubation with DNase for 20 minutes prior to addition of the TdT enzyme.

Table 2 below shows the motility of the sperm in the various lubricants, and shows the difference in motility of the sperm in the lubricants B10 to B14 and Pré™ as compared to the control lubricant G-IVF™ PLUS.

TABLE 2

Effects of preparations on motility in semen: Individuals and overall average

| Donor | Parameter | G-IVF | B10 | B11 | B12 | B13 | B14 | Pré |
|---|---|---|---|---|---|---|---|---|
| D017 | Motility (%) | 55.4 | 56.8 | 56.2 | 58.6 | 53.0 | 58.0 | 52.1 |
|  | S.D. (%) | 1.5 | 7.5 | 5.5 | 5.2 | 7.8 | 4.4 | 4.7 |
|  | Δ motility (%) |  | 1.4 | 0.8 | 3.2 | −2.4 | 2.6 | −3.3 |
| D019 | Motility (%) | 41.4 | 54.5 | 50.5 | 45.4 | 43.5 | 71.4 | 37.3 |
|  | S.D. (%) | 8.5 | 10.5 | 24.2 | 5.9 | 11.0 | 10.7 | 8.7 |
|  | Δ motility (%) |  | 13.1 | 9.1 | 4.0 | 2.1 | 30.0 | −4.1 |
| D022 | Motility (%) | 54.2 | 55.7 | 61.0 | 52.7 | 57.8 | 53.8 | 58.6 |
|  | S.D. (%) | 9.0 | 9.0 | 5.4 | 3.5 | 7.3 | 3.3 | 9.7 |
|  | Δ motility (%) |  | 1.5 | 6.8 | −1.5 | 3.4 | −0.4 | 4.4 |
| D030 | Motility (%) | 24.5 | 18.3 | 14.6 | ND | 15.7 | 14.1 | 10.6 |
|  | S.D. (%) | 10.8 | 4.1 | 5.0 | ND | 4.0 | 4.2 | 2.6 |
|  | Δ motility (%) |  | −6.2 | −9.9 | ND | −8.8 | −10.4 | −13.9 |
| D031 | Motility (%) | 43.0 | 38.3 | 35.6 | 39.5 | 35.2 | 32.6 | 23.1 |
|  | S.D. (%) | 0.8 | 2.8 | 0.8 | 4.9 | 0.3 | 3.2 | 0.2 |
|  | Δ motility (%) |  | −4.7 | −7.4 | −3.5 | −7.8 | −10.4 | −19.9 |
| D032 | Motility (%) | 16.6 | 15.3 | 15.7 | 17.9 | 15.7 | 21.0 | 17.9 |
|  | S.D. (%) | 2.3 | 7.8 | 5.8 | 4.4 | 9.8 | 5.8 | 2.6 |
|  | Δ motility (%) |  | −1.3 | −0.9 | 1.3 | −0.9 | 4.4 | 1.3 |
| D034 | Motility (%) | 50.0 | 58.2 | 46.3 | 49.7 | 54.4 | 53.3 | 46.8 |
|  | S.D. (%) | 3.0 | 8.3 | 10.5 | 3.2 | 5.0 | 11.7 | 6.0 |
|  | Δ motility (%) |  | 8.2 | −3.7 | −0.3 | 4.4 | 3.3 | −3.2 |
| DO35 | Motility (%) | 54.4 | 54.7 | 52.4 | 56.6 | 59.3 | 54.3 | 50.1 |
|  | S.D. (%) | 8.5 | 4.7 | 6.2 | 4.8 | 4.1 | 1.9 | 9.2 |
|  | Δ motility (%) |  | 0.3 | −2.0 | 2.2 | 4.9 | −0.1 | −4.3 |
| DO37 | Motility (%) | 23.3 | 28.7 | 34.2 | 28.3 | 30.4 | 35.0 | 19.8 |
|  | S.D. (%) | 2.7 | 1.3 | 6.1 | 5.4 | 7.0 | 3.0 | 5.2 |
|  | Δ motility (%) |  | 5.4 | 10.9 | 5.0 | 7.1 | 11.7 | −3.5 |
| DO38 | Motility (%) | 58.1 | 46.7 | 48.7 | 51.4 | 47.9 | 55.2 | 40.8 |
|  | S.D. (%) | 5.8 | 4.5 | 6.5 | 6.6 | 6.4 | 4.8 | 3.6 |
|  | Δ motility (%) |  | −11.4 | −9.4 | −6.7 | −10.2 | −2.9 | −17.3 |
| DO39 | Motility (%) | 65.3 | 59.5 | 62.3 | 63.0 | 67.3 | 67.0 | 58.0 |
|  | S.D. (%) | 6.1 | 6.9 | 5.5 | 5.7 | 12.2 | 2.4 | 14.6 |
|  | Δ motility (%) |  | −5.8 | −3.0 | −2.3 | 2.0 | 1.7 | −7.3 |
| D040 | Motility (%) | 65.9 | 66.1 | 73.3 | 65.7 | 67.2 | 68.1 | 59.8 |
|  | S.D. (%) | 7.2 | 9.8 | 6.7 | 3.5 | 5.7 | 4.5 | 10.1 |
|  | Δ motility (%) |  | 0.2 | 7.4 | −0.2 | 1.3 | 2.2 | −6.1 |
| D041 | Motility (%) | 61.4 | 64.5 | 65.7 | 55.1 | 37.3 | 51.8 | 31.2 |
|  | S.D. (%) | 10.1 | 6.8 | 5.5 | 12.9 | 20.8 | 5.6 | 25.2 |
|  | Δ motility (%) |  | 3.1 | 4.3 | −8.3 | −24.1 | −9.6 | −30.2 |
| D042 | Motility (%) | 54.1 | 54.1 | 56.3 | 44.6 | 45.3 | 51.4 | 34.5 |
|  | S.D. (%) | 4.4 | 7.2 | 10.4 | 5.3 | 7.7 | 10.5 | 7.4 |
|  | Δ motility (%) |  | 0.0 | 2.2 | −9.5 | −8.8 | −2.7 | −19.6 |
| DO43 | Motility (%) | 65.3 | 64.0 | 61.7 | 58.5 | 58.1 | 70.0 | 65.4 |
|  | S.D. (%) | 5.2 | 5.1 | 9.7 | 3.7 | 5.4 | 5.3 | 8.1 |
|  | Δ motility (%) |  | −1.3 | −3.6 | −8.8 | −7.2 | 4.7 | 0.1 |
| D046 | Motility (%) | 21.7 | 17.7 | 18.9 | 23.2 | 24.5 | 19.5 | 17.7 |
|  | S.D. (%) | 3.8 | 2.0 | 2.0 | 5.1 | 3.5 | 4.2 | 4.6 |
|  | Δ motility (%) |  | −4.0 | −2.8 | 1.5 | 2.8 | −2.2 | −4.0 |
| DO47 | Motility (%) | 71.3 | 60.8 | 64.5 | 59.7 | 64.8 | 66.0 | 50.4 |
|  | S.D. (%) | 5.2 | 6.1 | 1.1 | 4.5 | 5.2 | 3.0 | 9.0 |
|  | Δ motility (%) |  | −10.5 | −6.8 | −11.6 | −6.5 | −5.3 | −20.9 |
| DO48 | Motility (%) | 52.5 | 55.1 | 49.5 | 61.0 | 63.1 | 57.3 | 52.8 |
|  | S.D. (%) | 0.2 | 4.9 | 6.1 | 5.2 | 2.4 | 6.2 | 8.4 |
|  | Δ motility (%) |  | 2.6 | −3.0 | 8.5 | 10.6 | 4.8 | 0.3 |
| DO49 | Motility (%) | 63.4 | 67.9 | 67.5 | 61.8 | 66.3 | 71.9 | 62.9 |
|  | S.D. (%) | 6.7 | 4.5 | 9.5 | 2.9 | 2.3 | 4.2 | 10.9 |
|  | Δ motility (%) |  | 4.5 | 4.1 | −1.6 | 2.9 | 8.5 | −0.5 |

TABLE 2-continued

Effects of preparations on motility in semen: Individuals and overall average

| Donor | Parameter | "Preparation" | | | | | | |
|---|---|---|---|---|---|---|---|---|
| | | G-IVF | B10 | B11 | B12 | B13 | B14 | Pré |
| DO51 | Motility (%) | 57.4 | 52.0 | 62.0 | 51.2 | 61.8 | 65.1 | 51.8 |
| | S.D. (%) | 3.8 | 8.5 | 5.7 | 6.5 | 2.1 | 6.7 | 13.2 |
| | Δ motility (%) | | −5.4 | 4.6 | −6.2 | 4.4 | 7.7 | −5.6 |
| Average | Motility (%) | | −0.5 | −0.1 | −1.6 | −1.5 | 1.9 | −7.9 |
| | S.E. (%) | | 1.3 | 1.4 | 1.2 | 1.8 | 2.0 | 2.1 |
| | P | | 0.989 | 0.945 | 0.583 | 0.904 | 0.639 | 0.091 |

To determine if the response to preparations was different for sperm of poor quality compared to sperm of good quality, donors were clustered into low, medium and high motility groups and the average changes in motility compared (see Table 3 below).

TABLE 3

Effects of preparations on motility in isolated sperm: motility groups

| Motility group | Parameter | "Preparation" | | | | | |
|---|---|---|---|---|---|---|---|
| | | B10 | B11 | B12 | B13 | B14 | Pré |
| Low | Δ Motility (%) | 2.8 | 7.6 | 10.3 | 13.0 | 1.5 | 6.5 |
| | S.E. (%) | 2.6 | 1.4 | 2.4 | 4.4 | 1.9 | 3.6 |
| | P | 0.589 | 0.041 | 0.009 | 0.026 | 0.548 | 0.180 |
| Medium | Δ Motility (%) | −1.5 | −2.0 | 0.9 | −1.3 | 2.7 | 2.3 |
| | S.E. (%) | 1.9 | 3.8 | 3.3 | 4.9 | 3.0 | 4.2 |
| | P | 0.818 | 0.485 | 0.818 | 0.937 | 0.394 | 0.485 |
| High | Δ Motility (%) | −1.7 | 1.0 | 0.4 | 2.0 | 1.5 | −3.5 |
| | S.E. (%) | 1.2 | 1.2 | 1.4 | 1.7 | 2.5 | 4.3 |
| | P | 0.574 | 0.505 | 0.645 | 0.328 | 0.234 | 0.878 |

[a] individuals considered low motility if motility was <65% in isolated sperm [n = 6]
[b] individuals considered medium motility if motility was 65-80% in isolated sperm [n = 6]
[c] individuals considered high motility if motility was >80% in isolated sperm [n = 8]

In the low motility group of isolated sperm there was a significant increase in motility as a result of incubation with three of the preparations: B11, B12 and B13 which significantly improved motility by 7.6±1.4%, 10.3±2.4%, and 13.0±4.4% respectively (Table 3).

Further tests were carried out to establish if the preparations were toxic to sperm. The percentages of sperm with DNA damage following isolated sperm-preparation contact assays was assessed using the TUNEL assay. A control slide containing DNase added to isolated sperm incubated with G-IVF™ PLUS indicated that the assay was reliable with 99% of the sperm displaying signs of DNA damage. In contrast, no more than 2% of the sperm from any isolated sperm-preparation contact assay contained damaged DNA and appeared no different from the G-IVF™ PLUS control with no DNase.

The sperm motility test indicates that the current preparations are no more detrimental to sperm than the commercially available product, Pré. When mixed with semen or isolated sperm the preparations do not significantly reduce sperm motility or progressive motility. In fact, preparations B11, B12 and B13, which comprise a combination of HMW HA and LMW HA, provide motility enhancement to samples with low sperm motility.

Additional samples with improved stability were prepared in accordance with those in Table 1 with the inclusion of acid treated HA.

Further formulations were prepared using HMW HA and chitosan. The HMW HA used was eye drops grade or medical device grade having a molecular weight of 800,000 to 1,200,000, and was obtained from Novozymes A/S (Novozymes NS, Krogshoejvej 36, 2880 Bagsvaerd, Denmark. The chitosan had an estimated molecular weight of 10,000 to 500,000 and was obtained from FMC BioPolymer (FMC BioPolymer, 1735 Market Street, Philadelphia, Pa. 19103, USA). Chitosan with a viscosity of 20 to 200 mPa·s can also be used.

Formulations were prepared by combining the HA and chitosan in a clean 250 ml beaker to obtain 20.2 g of formulation. The so-formed mixture was stirred for one hour before being placed in sterile, labelled containers.

The formulations prepared are shown in Table 4.

TABLE 4

| Sample No | HA (g) | chitosan (g) | H$_2$O (g) |
|---|---|---|---|
| R0010 | 0.020 | 0.180 | 20.0 |
| R0011 | 0.040 | 0.160 | 20.0 |
| R0012 | 0.060 | 0.140 | 20.0 |
| R0013 | 0.080 | 0.120 | 20.0 |
| R0014 | 0.100 | 0.100 | 20.0 |
| R0015 | 0.120 | 0.080 | 20.0 |
| R0016 | 0.140 | 0.060 | 20.0 |
| R0017 | 0.160 | 0.040 | 20.0 |
| R0018 | 0.180 | 0.020 | 20.0 |
| R0019 | 0.200 | 0.000 | 20.0 |

Experiments were carried out to determine the stability of formulations R0010 to R0019. The rheological properties were tested using the frequency sweep shearing test. Frequency sweep of the sample was carried out considering a double concentric cylinder rheometer, with a gap of 500 μm, with geometry inertia of 17.95 μNm/s$^2$, at 25° C. A film of 7 ml was made around the inner cylinder and the frequency was varied from 0.6 to 250 rad/s. 5 ml samples were held in a 37°

C. water bath for 2 hours and the shearing test was carried out again. The shearing test was repeated three times for each sample.

Results of the shearing test experiment show that the dynamic viscosity decreases as the frequency increases from 0.6 to 250 rad/s. This shows that shear thinning is the main behaviour of the formulations.

With reference to FIG. 1, there is shown a graph which illustrates that the dynamic and complex viscosities of formulation R0012 decrease as the frequency increases.

TABLE 5

| Sample No | Dynamic viscosity (mPa·s) before thermal treatment | Dynamic viscosity (mPa·s) after thermal treatment | Viscosity reduction (%) |
|---|---|---|---|
| R0010 | 40.0 | 38.0 | 5.0 |
| R0011 | 45.0 | 42.0 | 6.7 |
| R0012 | 65.0 | 60.0 | 7.7 |
| R0013 | 68.0 | 65.0 | 4.4 |
| R0014 | 70.0 | 72.0 | NA |
| R0015 | 71.5 | 68.0 | 4.9 |
| R0016 | 72.0 | 64.0 | 11.1 |
| R0017 | 72.0 | 65.0 | 9.7 |
| R0018 | 75.0 | 60.0 | 20.0 |
| R0019 | 85.0 | 45.0 | 47.1 |

As can be seen from table 5, thermal treatment significantly reduces the viscosity of R0019 (which contains no chitosan (i.e., no LMW component)) and the addition of chitosan helps to maintain the visco-elasticity of formulations R0010 to R0018, which do contain chitosan.

In a further example, the formulations described above were provided with DNA in an amount between 0.1 and 1% by weight.

In a further example, the formulations described above were provided with benzethonium chloride in an amount between 23 and 38% by weight.

Furthermore, additional samples with improved stability were prepared in accordance with those in Table 4 with the inclusion of a LMW HA component.

Additional samples were prepared using high molecular weight HA having a molecular weight of 2,000,000 to 3,000,000 and were obtained from HTL Biotechnology (HTL, ZI de l'Aumaillerie, 35133 Javene, France).

Also, additional samples were prepared using high molecular weight HA having a molecular weight of 750,000 to 1,400,000, and obtainable from Novozymes A/S or similar suppliers.

Further samples were prepared using the low molecular weight component low molecular weight HA obtained from Kyowa having a molecular weight of 25,000 to 60,000, with and average molecular weight of 50,000.

Further samples were prepared using the low molecular weight component low molecular weight HA which was prepared from higher molecular weight HA using fermentation, heat degradation, free radical degradation and/or microwave treatment. For example, HA with an average molecular weight of around 2,000,000 was degraded to low molecular weight HA by using free radical depolymerisation with Fenton's reagent ($H_2O_2/Fe^{2+}$) to generate low molecular weight HA having a molecular weight of 5,000 to 200,000.

Another method used for preparing low molecular weight HA from higher molecular weight HA involved exposing the high molecular weight HA to dry heat at 100° C. for 15 minutes, which provided around a two to two and a half fold reduction in HA molecular weight. By adjusting the heating time, different molecular weight ranges are produced.

Further samples can be prepared using chitosan with a molecular weight of 1,000 to 750,000 and which can be obtained from FMC BioPolymer.

The invention of the present application provides a lubricant that has increased resistance to shearing forces, and which therefore can act as a lubricant for longer periods of time. Furthermore, the lubricant of the present invention acts to increase the motility of sperm, and in particular can be used to increase the motility of sperm with low motility. The present invention therefore has applications as a lubricant for improving, aiding or enhancing the chance of natural or artificial conception, and in particular, has utility in in vitro fertilisation treatment.

Further modifications and improvements can made to the invention as described herein without departing from the scope intended.

The invention claimed is:

1. A vaginal lubricant comprising high molecular weight hyaluronic acid (abbreviated "HA") having a molecular weight of 750,000 to 3,000,000 and a low molecular weight component having a molecular weight of 1,000 to 500,000 wherein the ratio of high molecular weight HA to the low molecular weight component is 9:1 w/w to 1:9 w/w, wherein the low molecular weight component is HA or chitosan and the lubricant has a viscosity of 2 to 1000 mPa·s.

2. The lubricant as claimed in claim 1 wherein the high molecular weight component has a molecular weight of 750,000 to 1,400,000.

3. The lubricant as claimed in claim 1 wherein the high molecular weight component has a molecular weight of 800,000 to 1,200,000.

4. The lubricant as claimed in claim 1 wherein the low molecular weight component has a molecular weight of 10,000 to 500,000.

5. The lubricant as claimed in claim 1 wherein the low molecular weight component has a molecular weight of 150,000 to 250,000.

6. The lubricant as claimed in claim 1 wherein when the low molecular weight component is HA, the ratio of high molecular weight HA to low molecular weight component is 3:1 w/w to 1:3 w/w.

7. The lubricant as claimed in claim 1 wherein when the low molecular weight component is chitosan, the low molecular weight component has an apparent viscosity of 20 to 200 mPa·s.

8. The lubricant as claimed in claim 1 having a pH of 6.5 to 7.4.

9. The lubricant as claimed in claim 1 comprising HA produced from the micro-organism *Bacillus subtilis*.

10. The lubricant as claimed in claim 1 comprising the high molecular weight HA, and wherein a proportion of the HA making up the low molecular weight component has been acid treated by de-acetylation of the HA in the acid to generate free amino groups.

11. The lubricant as claimed in claim 1 comprising DNA at a concentration of 0.1 to 1% by weight.

12. The lubricant as claimed in claim 1, wherein the lubricant does not comprise an anti-oxidant compound or composition.

13. The lubricant as claimed in claim 1, comprising medicaments useful in the treatment of sexually transferred diseases (STD).

14. The lubricant as claimed in claim 1, wherein the lubricant is in the form of a gel, foam, paste, liquid or spray.

15. A method of providing vaginal lubrication comprising the steps of applying the vaginal lubricant of claim 1 to the vagina of a patient in need thereof.

16. The method of claim 15 wherein the motility of sperm contacting the vaginal lubricant is maintained or increased.

17. The vaginal lubricant as claimed in claim 1 for use in therapy.

18. The vaginal lubricant as claimed in claim 1 for use in providing vaginal lubrication.

19. A method of promoting conception comprising the steps of applying the vaginal lubricant as claimed in claim 1 to the vagina of the patient in need thereof.

20. The vaginal lubricant as claimed in claim 1 for use in promoting conception.

21. A method of delivering a pharmaceutical or nutraceutical composition or the like comprising the steps of applying the vaginal lubricant as claimed in claim 1 to the vagina of a patient in need thereof.

22. The vaginal lubricant as claimed in claim 1 for use in delivering a pharmaceutical or nutraceutical composition or the like.

23. A method of manufacturing the vaginal lubricant as claimed in claim 1 comprising the steps of:
combining high molecular weight HA having a molecular weight of 750,000 to 3,000,000 and a low molecular weight component selected from HA or chitosan having a molecular weight of 1,000 to 500,000, wherein the ratio of high molecular weight HA to the low molecular weight component is 9:1 w/w to 1:9 w/w to provide the vaginal lubricant wherein the lubricant has a viscosity of 2 to 1000 mPa·s.

24. The method as claimed in claim 23 wherein the high molecular weight component has a molecular weight of 750,000 to 1,400,000.

25. The method as claimed in claim 23 wherein the high molecular weight component has a molecular weight of 800,000 to 1,200,000.

26. The method as claimed in claim 23 wherein the low molecular weight component has a molecular weight of 10,000 to 500,000.

27. The method as claimed in claim 23 wherein the low molecular weight component has a molecular weight of 150,000 to 250,000.

28. The method as claimed in claim 23 wherein the low molecular weight component has an apparent viscosity of 20 to 200 mPa·s.

29. The method as claimed in claim 23 wherein the vaginal lubricant comprises a vaginal lubricant comprising high molecular weight HA having a molecular weight of 750,000 to 3,000,000 and a low molecular weight component having a molecular weight of 1,000 to 500,000 wherein the ratio of high molecular weight HA to the low molecular weight component is 9:1 w/w to 1:9 w/w.

30. A product comprising the lubricant as claimed in claim 1.

31. The product as claimed in claim 30, comprising a device selected from the group consisting of in a single use pre-filled syringe and a spray container with a single use nozzle.

* * * * *